Jan. 2, 1973 J. T. IRWIN Plant Pat. 3,285
KALANCHO PLANT
Filed April 13, 1971
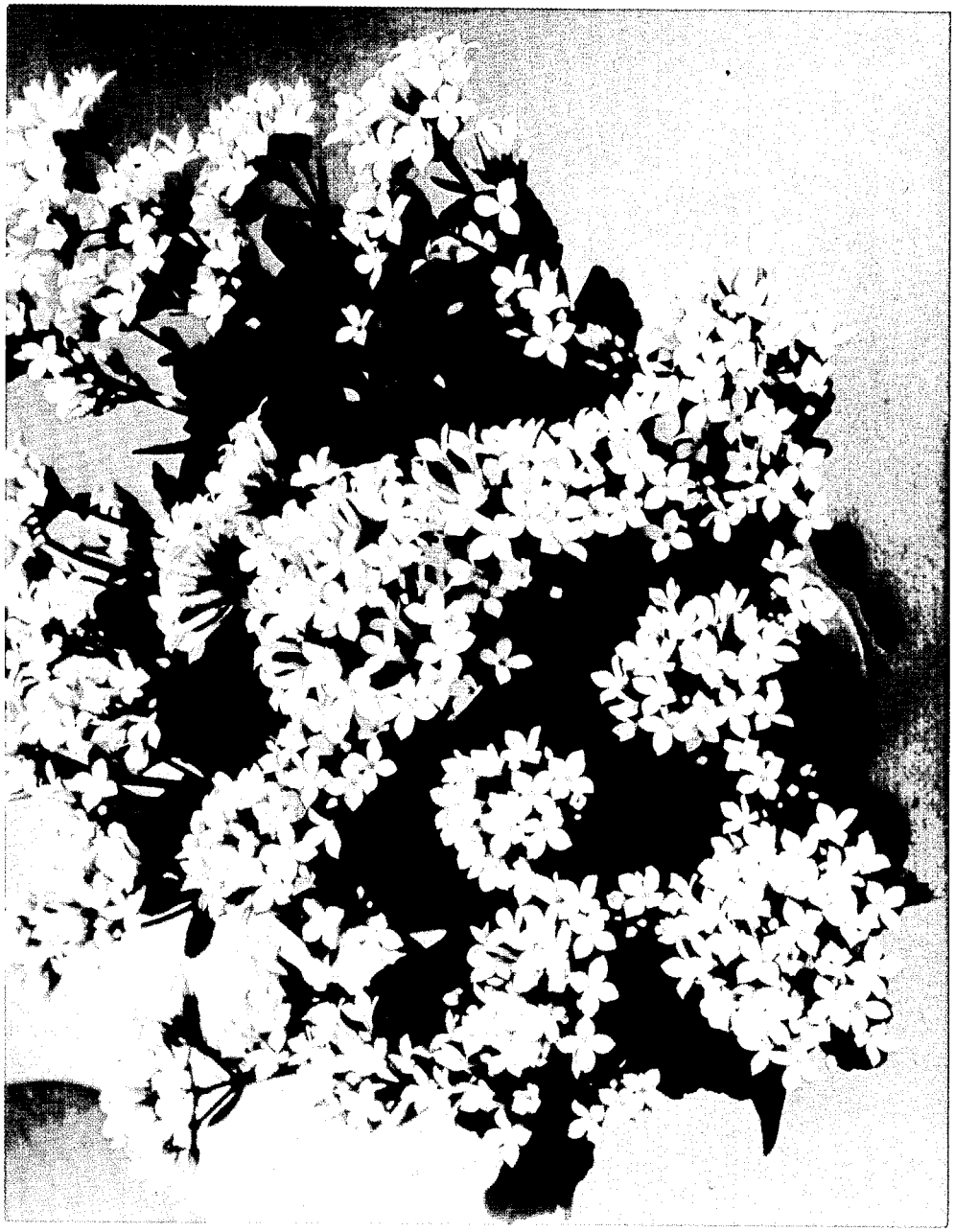
Inventor.
James T. Irwin
By: Robb & Robb
Attorneys.

United States Patent Office

Plant Pat. 3,285
Patented Jan. 2, 1973

3,285
KALANCHOE PLANT

James T. Irwin, Canyon, Tex., assignor to Irwin Greenhouses, Inc., Canyon, Tex.

Filed Apr. 13, 1971, Ser. No. 133,769
Int. Cl. A01h 5/00
U.S. Cl. Plt.—68 1 Claim The present invention relates to a new and distinct variety of kalanchoe plant which was discovered by me as a cultivated sport of the kalanchoe variety known as "Exotic" (patent pending), said discovery having been made by me in one of my greenhouses maintained at Canyon, Tex.

At the time of my discovery, various varieties of kalanchoe plants, including several thousand plants of the variety "Exotic" which had been previously originated by me in my greenhouses located in Randall County, Tex., were being commercially grown under my personal direction and care. In the course of these growing operations, my attention was attracted to one particular plant among those of "Exotic" which bore flowers of apricot color instead of the normal soft orange flower color typical of the flowers of "Exotic." Close inspection of this particular plant showed that it had sported a single branch and flowering stem which bore the flowers to which my attention had been originally attracted, and I accordingly took steps to carefully preserve the sport and keep it under close observation. In due course, I asexually reproduced the sport by direct rooting of stem tip cuttings, as performed by me in my greenhouses aforesaid. Continued observations and tests of the original sport and its progeny derived therefrom as indicated in the foregoing fully confirmed that the apricot flower color comes true and remains stable as a unique and distinctive kalanchoe flower color, combined with additional features which are outstanding and which, on the whole, represent a unique combination of the following principal features which distinguish my new sport from its parent "Exotic" as well as from all other kalanchoe varieties of which I am aware:

(1) A highly branched and upright habit of growth;

(2) Medium sized and flexible foliage of moss green to fern green color;

(3) A uniform and consistent plant height and bloom date;

(4) An ability to initiate and develop flower buds under high night temperatures of summer when other varieties fail;

(5) A profuse blooming habit, with the ability to respond to short day treatment and with consequent capability of year-around flowering;

(6) A distinctive, attractive and uniform apricot flower color;

(7) Superior resistance to root rot as compared with most other varieties; and (8) Long-lasting qualities as a potted plant.

The accompanying drawing shows a typical specimen plant of my new kalanchoe variety as depicted in bloom and in color as nearly true as it is reasonably possible to make the same in an illustration of this character.

The following is a detailed description of my new kalanchoe variety, with color terminology in accordance with Maerz and Paul Dictionary of Color, except where general color terms of ordinary dictionary significance are obvious:

Parentage: Sport of "Exotic" (patent pending).

Propagation: Holds its distinguishing characteristics through succeeding propagations by direct rooting of stem tip cuttings.

Locality where grown and observed: Randall County, Tex.

Plant:

*Form.*—Much-branched; upright; compact.

*Growth habit.*—Medium vigorous; upright; branching; compact.

*Rooting habit.*—Numerous and fibrous roots; roots easily from any part of stem.

*Blooming habit.*—Compound umbel.

*Blooming season.*—Normally about December 8, but suitable for forcing into year-around bloom by manipulating long and short days under suitable greenhouse conditions.

Foliage:

*Size.*—Medium. Length—about 3 to 4 inches long. Width—about 2½ inches.

*Quantity.*—Normal abundance.

*Color.*—New foliage—upper side—Green, No. 83—. Under side—Green, No. 82+. Old foliage—upper side—Green, No. 83—. Under side—Green, No. 82+.

*Shape.*—Oval. Base—from obtuse to acute. Tip—obtuse.

*Texture.*—Upper side—Glossy; smooth. Under side—smooth.

*Margin.*—Crenate.

*Aspect.*—Glossy.

Disease resistance: Much more resistant to root rot than former kalanchoe varieties, as determined by comparison with many other varieties as grown in greenhouses under the same conditions in Randall County, Tex.

Flowers: Perfect.

*Size.*—From about ⅝ inch to ⅞ inch in diameter and about ¾ inch deep; petals about 11/32 inch long and about ¼ inch wide.

*Form.*—Perigynous; section petals united; ovary inferior.

*Color.*—Uniform. Upper side of petals—Apricot, No. 11. Under side of petals—Color No. 16+

*Blooming period.*—From 4 to 6 weeks.

Hardness: Good; has successfully withstood temperatures of 35° F. in central New Mexico, and 105° F. in Canyon, Tex.

General observations: Very attractive even with only a few flowers open; flowers form a massive flower head composed of hundreds of individual flowers at maturity and retain their fresh appearance while doing so; under side of leaves take on a bronze cast under high sunlight conditions; flowers are slightly larger than those of "Exotic," as well as differing from the latter by their uniform apricot color.

I claim:

1. A new and distinct variety of kalanchoe plant, substantially as herein shown and described, characterized particularly as to novelty by the unique combination of a highly branched and upright habit of growth, medium sized and flexible foliage of moss green to fern green color, a uniform and consistent plant height and bloom date, an ability to initiate and develop flower buds under high night temperatures of summer when other varieties fail, a profuse blooming habit, with the ability to respond to short day treatment and with consequent capability of year-around flowering, a distinctive, attractive and uniform apricot flower color, superior resistance to root rot as compared with most other varieties, and long-lasting qualities as a potted plant.

No references cited.

ROBERT E. BAGWILL, Primary Examiner